United States Patent
Har-Shai et al.

(10) Patent No.: US 6,200,318 B1
(45) Date of Patent: Mar. 13, 2001

(54) KIT FOR STERNUM FIXATION IN CHEST SURGERY

(75) Inventors: Yaron Har-Shai; Roni Ammar, both of Haifa (IL); Pertti Tormala, Tampere (FI)

(73) Assignee: Technion Research and Development Foundation, Ltd., Haifa (IL)

( * ) Notice: Subject to any disclaimer, the term of this patent is extended or adjusted under 35 U.S.C. 154(b) by 0 days.

(21) Appl. No.: 09/403,064

(22) PCT Filed: Apr. 1, 1998

(86) PCT No.: PCT/IL98/00158

§ 371 Date: Apr. 17, 2000

§ 102(e) Date: Apr. 17, 2000

(87) PCT Pub. No.: WO98/44850

PCT Pub. Date: Oct. 15, 1998

(51) Int. Cl.[7] .................................................. A61B 17/82
(52) U.S. Cl. .............................. 606/74; 606/77; 606/102; 606/105; 606/139; 606/213; 140/123.6
(58) Field of Search .................................. 606/74, 77, 102, 606/103, 105, 139, 142, 157, 213, 215, 216, 218; 140/123.5, 123.6

(56) References Cited

U.S. PATENT DOCUMENTS

| | | |
|---|---|---|
| 2,291,413 | 7/1942 | Siebrandt . |
| 5,339,870 | 8/1994 | Green et al. . |
| 5,355,913 | 10/1994 | Green et al. . |
| 5,395,374 | 3/1995 | Miller et al. . |

OTHER PUBLICATIONS

D. J. Perkins et al., Secondary sternal repair following median sternotomy using interosseous absorbable sutures and pectoralis major myocutaneous advancement flaps, *British Journal of Plastic Surgery*, vol. 49, 1996, pp. 214–219.

Seppo Santavirta et al., Immune Response to Polyglycolic Acid Implants, *The Journal of Bone and Joint Surgery*, vol 72–B, No. 4, Jul. 1990, pp. 597–600.

Duane E. Cutright, DDS, Ph.D. et al., Fracture reduction using a biodegradable material, polylactic acid, *Oral Surgery*, vol. 29, Jun. 1971, pp. 393–397.

O. M. Bostman, M.D., Current Concepts Review Absorbable Implants for the Fixation of Fractures, *The Journal of Bone and Joint Surgery*, vol. 73–A, No. 1, Jan. 1991, pp. 148–153.

Timo Pohjonen et al., In vitro hydrolysis of self–reinforced polylactide composites, *Medical & Biological Engineering & Computing*, vol. 34, Supplement 1, Part 1, 1996, pp. 127–128.

Harry S. Soroff, M.D. et al., Improved Sternal Closure Using Steel Bands: Early Experience With Three–Year Follow–up, *The Society of Thoracic Surgeons*, 1996, pp. 1172–1176.

Steven C. Hendrickson, M.D. et al., Sternal Plating for the Treatment of Sternal Nonunion, *The Society of Thoracic Surgeons*, 1996, pp. 512–518.

Wen Cheng, M.D., Biomechanical Study of Sternal Closure Techniques, *The Society of Thoracic Surgeons*, 1993, pp. 737–740.

*Primary Examiner*—Michael Buiz
*Assistant Examiner*—David O. Reip
(74) *Attorney, Agent, or Firm*—Knobbe, Martens, Olson & Bear, LLP

(57) ABSTRACT

A tool kit for use in the inducement of the reconstitution and healing of the sternum after an operation on a patient in the chest region in which during the operation the sternum is cut into two hemisterna. The kit serves for the post-operational approximation and fixation of the hemisterna in a position which enables their spontaneous growing together. The kit includes an approximation tool for the application of a selected force to the hemisterna to brig them into reconstituted configuration, and a set of clamping apparatus for firmly locking the hemisterna in the reconstituted configuration. The clamping apparatus is made of a non-immunogenic polymeric material that is readily degraded in the patient's body to yield degradation products readily absorbed by the patient's body.

9 Claims, 6 Drawing Sheets

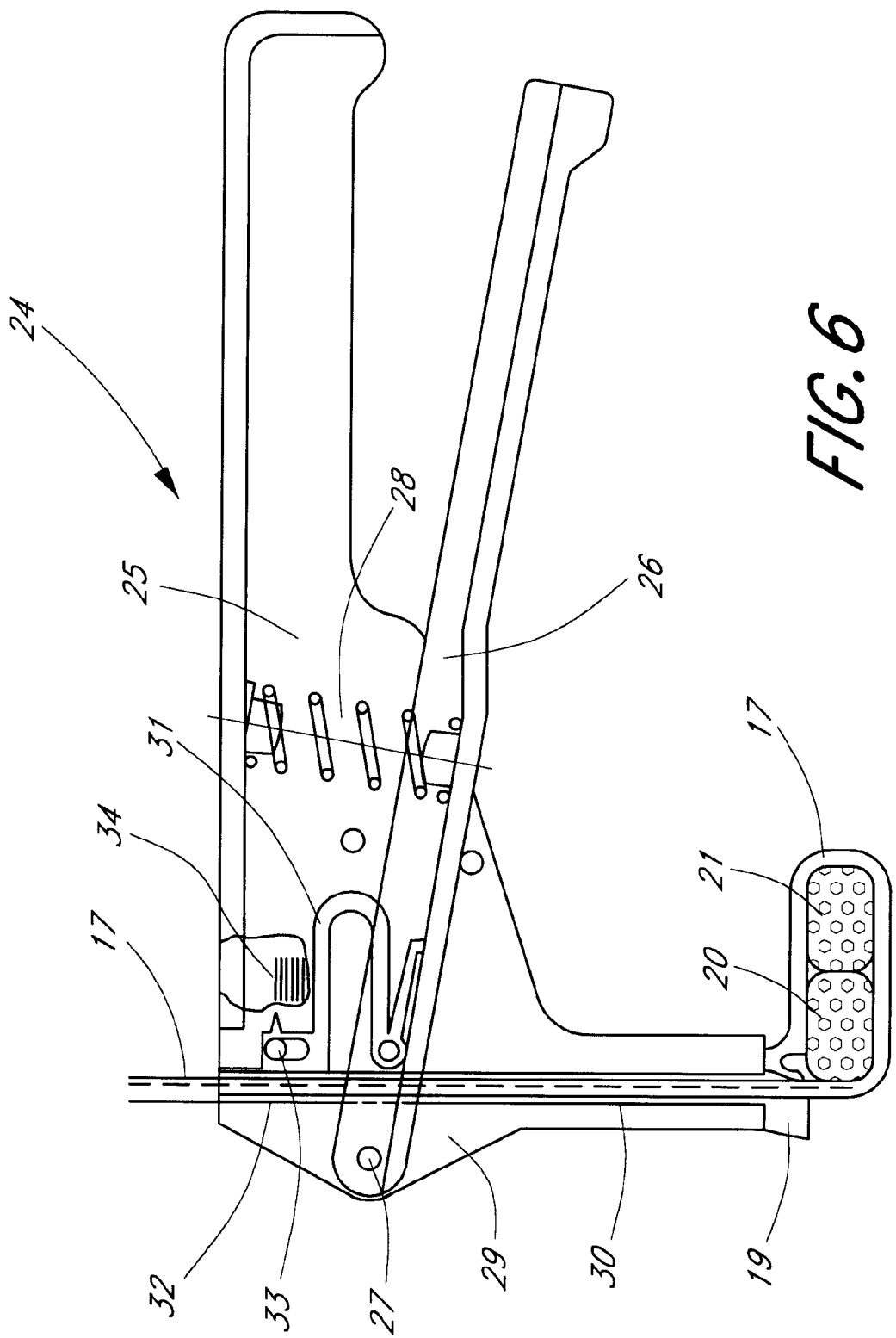

KIT FOR STERNUM FIXATION IN CHEST SURGERY

This application is the U.S. National Phase under 35 U.S.C. § 371 of International Application PCT/IL98/00158, filed Apr. 1, 1998.

FIELD OF THE INVENTION

The present invention concerns surgical means for approximating bone fragments of the sternum and fixing them in a biologically safe manner ultimately facilitating good functional reconstitution of the original structure.

BACKGROUND OF THE INVENTION AND PRIOR ART

Chest surgery such as, for example, open heart surgery requires opening of the chest and rib cage in order to facilitate access to the organ to be operated. The front central part of the rib cage constitutes a longitudinal bone, the sternum, which overlies the heart and secures the ribs. A specific action performed in such surgery is longitudinal sectioning of the sternum into two halves ("median sternotomy"). After performing the heart surgery, the chest is closed as a part of a reconstitution operation, in which among other activities the sternum bone halves are brought to union and secured together by mechanical means.

Post operative complications in the healing of the sternum are not uncommon, resulting from several reasons. Especially troublesome is the constant movement associated with the breathing cycle, to which the bone is subjected, which keeps the sternum in a cyclic strain regime often accompanied by unpredicted mechanical stresses. Such strains may eventually cause nonunion or breakage of the bone. Nowadays as recuperating procedures for cardiac therapy have become more common, sternal complications have been increasing likewise. Healing disorders can be expected to occur more commonly in patients suffering from bone disorders such as excessive porosity.

None of the common traditional methods as well as the newer ones pertaining to this specific type of surgery have so far proved to insure adequate degree of sternum healing in such type of operations. A discussion of methods for sternal closure-techniques is elaborated by Cheng W. et al. (Biomechanical Study of Sternal Closure Techniques. *Ann Thorac Surg.* 55:737-40, 1993). Although the authors maintain that wire approximation and tensioning is the method of choice, present medical observations indicate this method to be risky with many complications which arise from inadequate fixation of the bones and interference of the artificial insertions in the physiological make up of the body. Hendrickson S. C. et al (Sternal Plating for The Treatment of Sternal Nonunion. *Ann. Thorac Surg.* 62:512-8, 1996), provide evidence for the superior effectivity of tension bands or plates in securing sternal fragments postoperatively. According to such technique, the bands or plates are made out of stainless steel and as such may require special care or even specific surgery for removal. The use of steel bands instead of wire for closure of sternum halves (called also hemisterna) has been shown to provide better results than wire closures also with respect to pain and duration of hospitalization (Soroff H. S. et al. Improved Sternal Closure Using Steel Bands: Early Experience With Three-Year Follow-up. *Ann. Thorac Surg.* 61:1172-6, 1996). Green D. T. et al. (U.S. Pat. No. 5,339,870) disclose a mechanical device for providing mechanized method and apparatus which utilizes flexible strap for retaining and securing hemisterna. The same authors disclose in a different publication (U.S. Pat. No. 5,355,913) a mechanical system for retaining and securing split tissue for surgical reconstruction. In this patent an additional feature is disclosed according to which a disengaging mechanism in the mechanical driving gear provides a means for applying an upper limit to the force applied.

Generally, the shortcomings of the present practices are a combination of all or a part of the following: infections caused by metal or plastic parts intentionally left in the bone or surrounding it, cutting effect exerted by tension stitches left intentionally in the body, pain and aesthetic aspects. The consequences of insufficient or superfluous force applied for the approximation and securing together the two hemisterna, may also be detrimental to the healing process.

Plastic materials made out of biologically benign α-hydroxy acids (Pohjonen T. and Tormala, P. In Vitro Hydrolysis of Self-Reinforced Polylactide Composites. 1996. Medical & Biological Engineering & Computing 34 Supplement 1, Part 1.) have been used in the bone fixation in the form of implants (Bostnan O. M., Curt Concepts Review: Absorbable Implants for the Fixation of Fractures. *J. Bone Joint Surg.* 73-A (1)148–152, 1991) or degradable sutures (Cutright D. E. et al. Fracture Reduction using a Biodegradable Material, Polylactic acid. *J. Oral Surg.* 29: 393–397, 1971), have revealed good potential for tissue repair and specifically bone fixation. The immune response in the body to such material is negligible, although mild, non specific reactions to the plastic do occur (Santavarita S. et al. Immune response to polyglycolic Acid Implants. *J. Bone Joint Surg.* [Br] 72-B:597–600, 1990).

Polydioxanone, which degrades in the body first to glycolic acid is used as a building block for production of bioabsorbable plastic (Bostman O. M., Current Concepts Review: Absorbable Implants for the Fixation of Fractures. 1991. *J. Bone Joint Surg.* 73-A (1)148–152.). Perkins D. J. et al (Secondary Sternal Repair Following Median Sternotomy using Interosseous absorbable Sutures and Pectoralis Major Myocutaneous Advancement Flaps. *British Journal of Plastic Surgery* 49:214–219, 1996), used polydioxanone sutures to achieve sternal repair with excellent therapeutic and aesthetic results.

The use of bioabsorbable plastic straps in surgery for joining split tissue was disclosed (Green D. T. et al. U.S. Pat. No. 5,355,913) as a possible alternative building material in the manufacturing of tissue repair devices. The same authors in U.S. Pat. No. 5,339,870 disclosed a device for applying a buckle assembly that secures a strap in a loop around a split tissue such as a split sternum.

SUMMARY OF THE INVENTION

It is the object of the present invention to provide for the purpose of inducement of the reconstitution and healing of the sternum after an operation in the chest region in which the sternum is cut longitudinally along a cutting line into two hemisterna having each a cut edge, improved means for the approximation of the hemisterna so as to bring them into a reconstituted configuration at which their cut edges bear on each other, and for the fixation of the hemisterna in such position so as to enable their growing together.

The present invention provides for use in the inducement of the reconstitution and healing of the sternum after operation of a patient in the chest region in which operation the sternum is cut into two hemisterna, a tool kit for the approximation and fixation of the hemisterna in a position which enables their spontaneous growing together, which tool kit comprises:

(i) an approximator tool for the application of a selected force to the hemisterna to bring them into a reconstituted configuration; and (ii) a set of clamping means designed for firmly locking the hemisterna in said reconstituted configuration, which clamping means are made of a non-immunogenic polymeric material that is readily degraded in the patient's body to yield degradation products readily absorbed by the patient's body.

A typical type of operation in the chest region in which the tool kit according to the invention is used is open heart surgery.

Preferably, the said approximator tool is fitted with gauge means for measuring the applied force which is selected in accordance with certain characteristica of the patient such as size, weight, age and sex.

In accordance with one embodiment the approximator tool is designed to hold and tighten the clamping means whereby the operations of approximation and clamping are combined.

In accordance with another embodiment of the invention the approximator tool is designed only for bringing together the hemisterna into a reconstituted configuration and the clamping means are applied separately.

In either embodiment, once the clamping means have been applied and tightened, the approximator tool is withdrawn.

The clamping means in a tool kit according to the invention may be flexible, e.g. in form of a band, belt or strap, or rigid with a measure of resilience, e.g. in form of clamps made of a single body or of interlocking parts. The size of the clamping means is so selected that their full decomposition is completed only when the healing process has progressed to an extent that the sternum is no longer spontaneously split along the cutting line.

BRIEF DESCRIPTION OF THE DRAWINGS

For better understanding of the invention, some specific embodiments will now be described with reference to the annexed drawings in which:

FIG. 6 shows an approximator tool according to the invention also serving for the application and tightening of a strap of the kind shown in FIG. 3;

DESCRIPTION OF SPECIFIC EMBODIMENTS

Typically, the clamping and fixation means according to the invention are made of polymerized a-hydroxy carboxylic acids such as, for example, polylactic acid, which hydrolyze gradually in the body down to the benign monomer building block, the size of the clamping means being so selected that they are on the one hand not fully degraded before the healing process of the sternum has progressed sufficiently to avoid any spontaneous fissure along the cutting line, and on the other hand they do not stay undissolved in the body for too long a time in order not to elicit a reaction against foreign bodies (Bostman, O., et al., Foreign Body Reactions to Fraction Fixation Implants of Biodegradable Synthetic Polymers, *J. Bone Joint Surg.,* 72B:59206, 1990). Such selection, similar as the selection of the applicable force for bringing together the hemisterna, is a function of various parameters such as the patient's size, weight, age and sex.

Also preferably, there are provided in accordance with the invention empirical data to guide the user to the selection of the applicable force and to the appropriate size of the clamping means in accordance with the said parameters.

Figure 2:
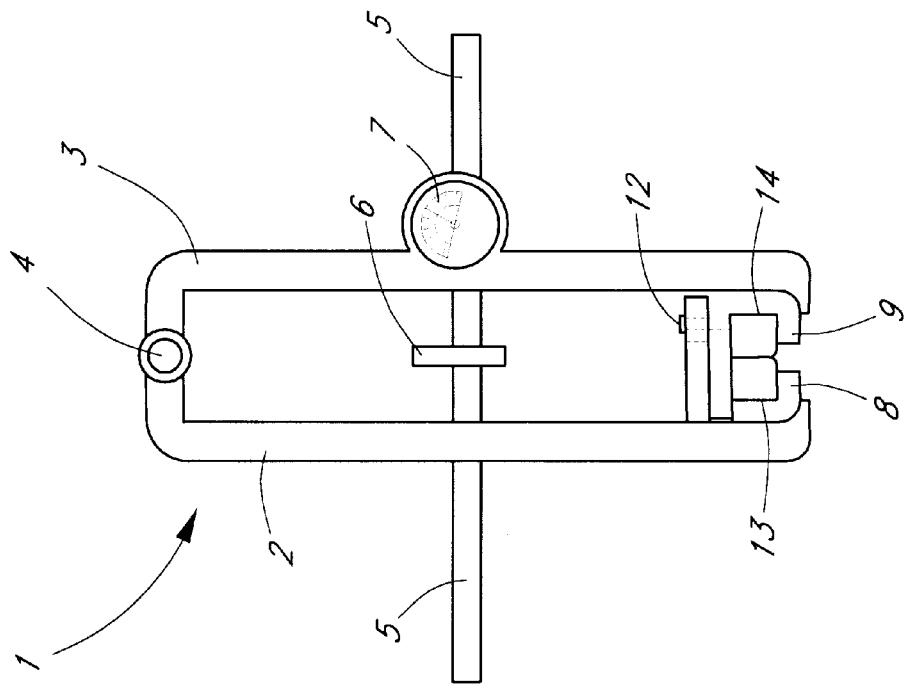
FIG. 2 shows the tool of FIG. 1 in the gripping state.
Figure 1:
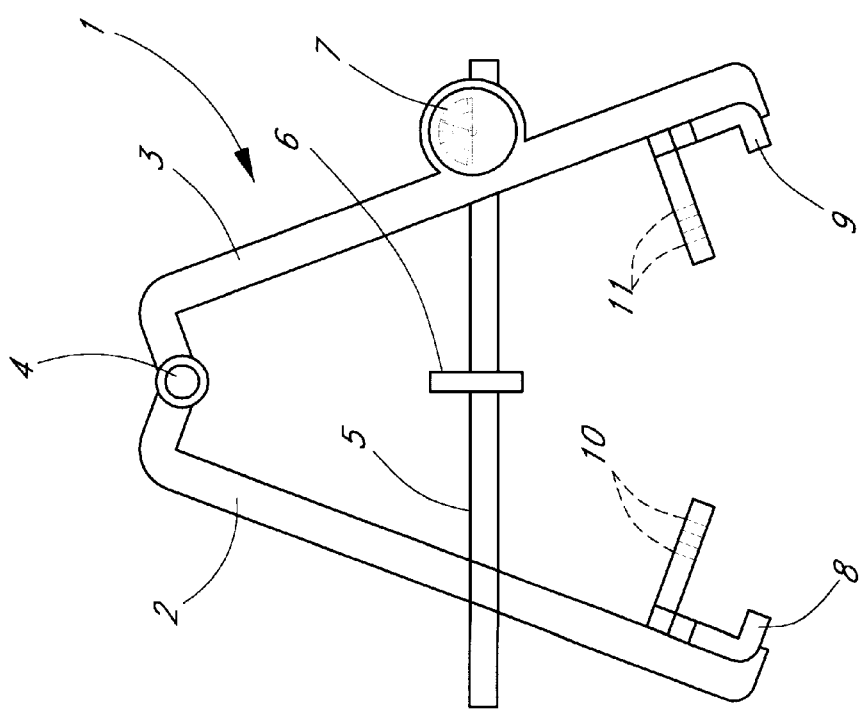
FIG. 1 shows one embodiment of an approximator tool according to the invention in the spread state.

Turning now to FIGS. 1 and 2, there is shown a forceps-type approximator tool 1 with arms 2 and 3 pivoted together at 4 and whose spread is adjustable by means of a screw threaded bolt 5 integral with arm 2 and screwingly engaging a gauge 7 integral with arm 3. Bolt 5 is fitted with an integral knob 6 by which the bolt is turned whereby the spread of ams 2 and 3 is increased or decreased, as the case may be.

Near their gripping ends, arms 2 and 3 carry complementary hemi-clamps 8 and 9. The hemi-clamp 8 has two screw-threaded bores 10 and the hemi-clamp 9 has two screw-threaded bores 11. In the gripping state shown in FIG. 2, bores 10 and 11 are in alignment and one aligned pair of bores is engaged by a screw 12. Different combinations between bores 10 and 11 are possible in dependence on the applied gripping force. It is noted, moreover, that the upper flanges of the hemi-clamps 8,9 may each comprise a larger number of screw-threaded bores which can be brought into alignment in various combinations whereby provision is made for the selection of a larger number of degrees of gripping force.

In operation, the approximator device 1 is brought from the spread state of FIG. 1 into the gripping state of FIG. 2, whereby the hemi-clamps 8 and 9 are brought into inter-engagement while embracing the two hemisterna 13 and 14. Once the desired force has been applied and at least one screw-threaded bore 10 of the flange of the hemi-clamp 8 is brought into alignment with at least one of the two screw-threaded bores 11 in the flange of the hemi-clamp 9, a screw 12 is screwed into at least one pair of aligned bores 9,10, following which the approximator device is brought back into the spread state, free, however, of the hemi-clamps 8 and 9 which remain on the sternum.

The clamping assembly 8,9,12 is made of a degradable material such as a polymerized α-hydroxy carboxylic acid and as the healing process progresses, the clamping assembly is degraded by hydrolysis and eventually disappears altogether.

Figure 3:
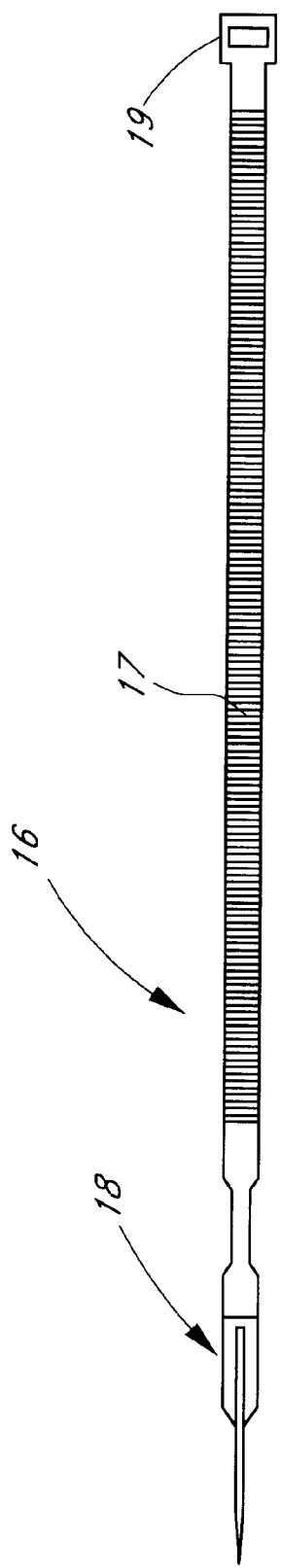
FIG. 3 shows a clamping and fixing device according to the invention in form of a flexible, corrugated strap.
Figure 5:
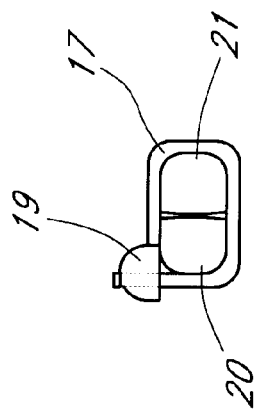
FIG. 5 shows in cross section two hemisterna held together by a strap according to FIG. 3.
Figure 4:
FIG. 4 is a fragmentary elevation of the strap in the tool of FIG. 3, drawn to a larger scale.

Turning now to FIGS. 3 to 5, there is shown a clamping device 16 according to the invention in the form of a flexible, corrugated strap 17 having a pointed head portion 18 and at the rear a buckle 19. As shown in FIG. 4, the corrugation is ratchet-like and it is easily understood that a suitable tooth in buckle 19 (not shown) is capable of firmly engaging the corrugated strap. The method in which strap 17 holds together two hemisterna 20 and 21 is shown in FIG. 5 and it is seen there that buckle 19 engages the wound and tightened strap with the tip portion 18 and any excess length of the strap 17 having been cut off.

Attention is now directed to FIG. 6 which shows an approximator tool 24 designed for the application of the corrugated strap of FIG. 3. Tool 24 has grips 25 and 26 pivotally connected to each other at 27 and biased into the spread state by a helical spring 28. As shown, grip 25 has an integral head portion 29 having a through going groove 30 accommodating excessive length of strap 17. A double bent, U-shaped leaf spring 31 anchored at one end in grip 26 has a butt end 32 bearing on strap 17 in groove 30 and having means capable of gliding on the ratchet-type corrugations of strap 17 when tool 24 is compressed thereby releasing strap 17, and engaging the strip when grip 25 is released thereby pulling strap 17 upward (with reference to FIG. 6) and tightening it around hemisterna 20,21. Butt end 32 is fitted with a pointer 33 associated with a gauge 34, indicating the cumulative tightening force by which the hemisterna 20,21 are pressed together.

In operation, a loose loop of strap 17 is formed manually by winding strap around the hemisterna 20 and 21 and threading the tip 18 (FIG. 3) through buckle 19 which is then followed by threading the strap into groove 30 of the approximator 24. The strap is now tightened by a succession of compressions of approximator 24 whereby, as explained, strap 17 is pulled and tightened around the hemisterna 20,21, and when the desired force has been applied as shown by the indication appearing opposite pointer 33, the tightening operation is interrupted, the excessive strap 17 is cut off and the approximator 24 is removed, all of which leads to the configuration of FIG. 5.

Figure 7:
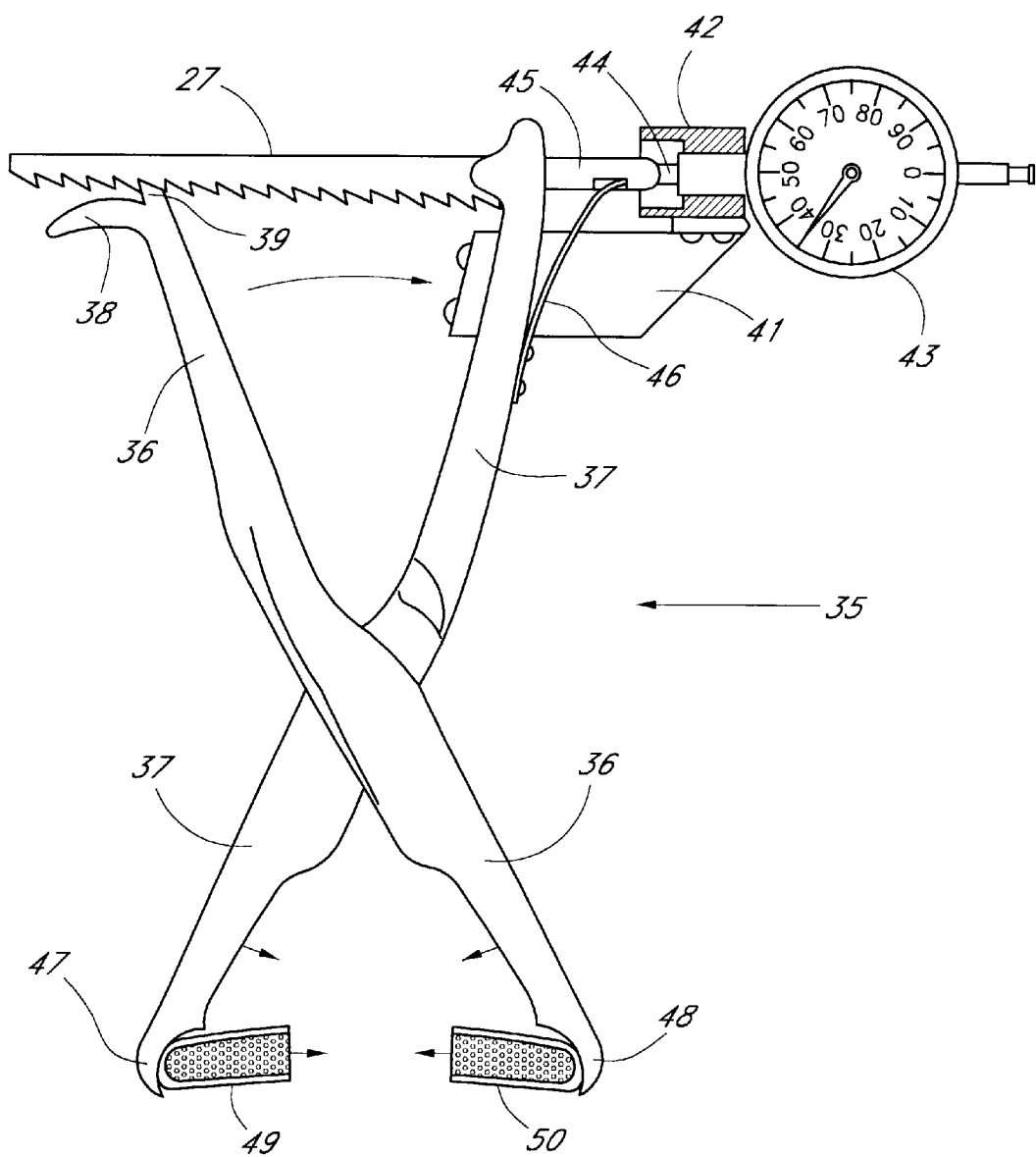
FIG. 7 shows another embodiment of an approximator tool according to the invention.

Attention is now directed to FIG. 7 which shows another, scissor-type approximator device according to the invention. As shown, the approximator 35 comprises arms 36 and 37 pivoted at their center regions (the pivot is not seen in FIG. 7). Arm 36 has a foot 38 fitted with a tooth 39 engaging ratchet bar 40 in the manner shown. Arm 37 comprises a bracket 41 holding a sleeve 42 forming part of a gauge 43 and comprising a pin 44 cooperating with a smooth end portion 45 of ratchet bar 40. A sensor spring 46 mounted on arm 37 engages end portion 45 of ratchet bar 40.

Figure 8:
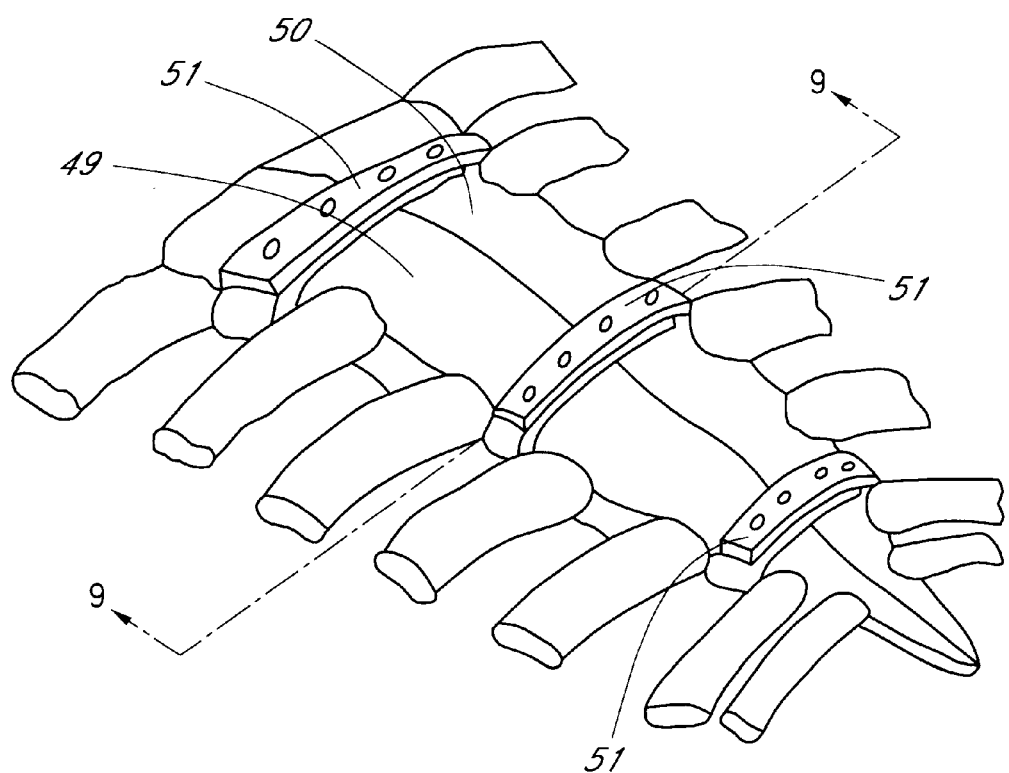
FIG. 8 is a perspective view of hemisterna in a reconstituted sternum configuration held together by three clamps according to the invention.

In operation, the pointed gripping ends 47,48 of the approximator 35 are inserted into the intercostal spaces (i.e. between adjacent ribs) so as to grip the two hemisterna 49 and 50 shown in FIG. 8, which are then brought together by pressing together the arms 36 and 37. During the compression tooth 39 glides on the ratchet of bar 40 and the cumulative force is read on gauge 43. When the desired force is reached compression is interrupted and the approximator is arrested by tooth 39 engaging the ratchet. At this stage a clamp 51 is applied and fixed and the approximator tool 35 is then removed.

Figure 9:
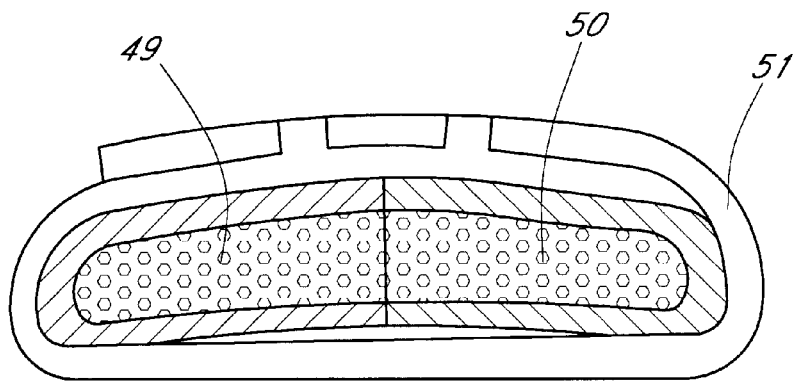
FIG. 9 is a section along line IX—IX of FIG. 8.

The final reconstitution configuration is shown in FIGS. 8 and 9, the latter being a section along line IX—IX of the former. As shown, in this particular case, the hemisterna are held together by three clamps 51.

Figure 10:
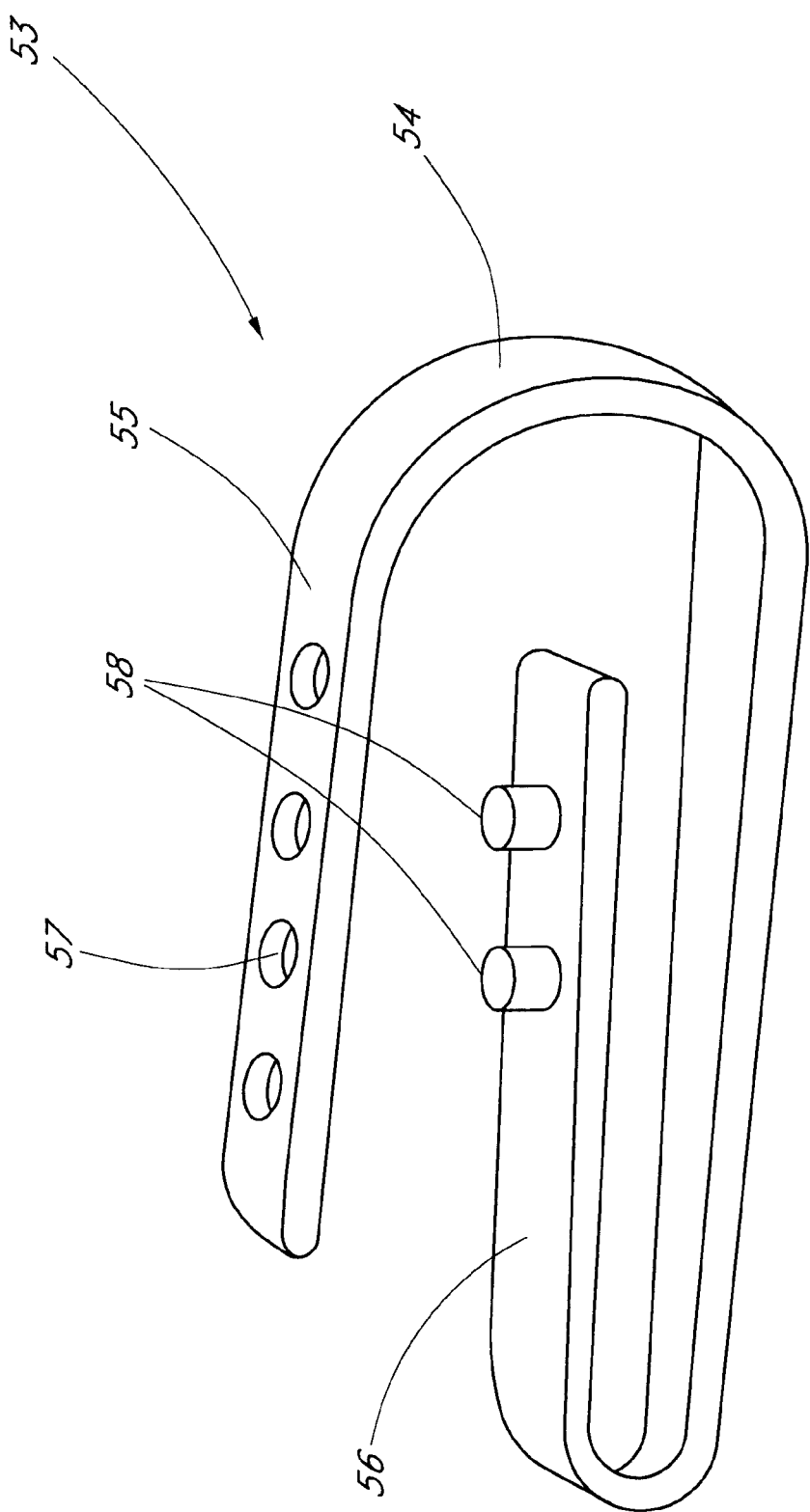
FIG. 10 is a perspective view of a clamping device according to the invention.

Attention is now directed to FIG. 10 which shows in perspective an embodiment of a solid clamp according to the invention which is made of one single, resilient piece. As shown, the clamp 53 is in form of a double bent solid resilient strap-shaped sheet 54 having upper and medium arms 55 and 56, the former having four holes such as hole 57 and the latter having two pins 58 fitting tightly into the holes of ann 55.

Clamps of FIG. 10 can be used in conjunction with a device according to FIG. 7. Once the two hemisterna 49,50 are brought together, clamps 53 are slid into intercostal spaces other than the one gripped by the tool 35, and arms 55 and 56 are pressed together whereby the pair of pins 58 engage in tight fit any desired pair of adjacent holes in arm 55.

What is claimed is:

1. A tool kit for the approximation and fixation of the hemisterna in a position which enables their spontaneous growing together after an operation in which the sternum is cut into two hemisterna, said tool kit comprising:

(i) an approximator tool for the application of a selected force to the hemisterna to bring them into a reconstituted configuration, wherein said approximator tool comprises a gauge for measuring said force; and (ii) a set of clamps designed for firmly locking the hemisterna in said reconstituted configuration, said clamps comprising a non-immunogenic polymeric material that is readily degraded in the patient's body to yield degradation products readily absorbed by the patient's body.

2. A tool kit according to claim 1, wherein said approximator tool is designed to hold and tighten the clamps whereby the operations of approximation and clamping are combined.

3. A tool kit according to claim 1, wherein said approximator tool is designed for bringing together the hemisterna into a reconstituted configuration and the clamps are applied separately.

4. A tool kit according to claim 1, wherein said clamp is a flexible member selected from the group consisting of: flexible bands, belts and straps.

5. A tool kit according to claim 4, wherein said clamp is corrugated and comprises a buckle for threading across a portion of said flexible member, wherein said buckle is capable of gripping a part of said flexible member accommodated therein.

6. A tool kit according to claim 1, comprising an approximator tool having in combination:

an assembly of two handles pivoted to each other and biased into a spread state;

a groove for accommodating a length of a flexible corrugated clamp; and a butt capable of engaging said flexible corrugated clamp within said groove.

7. A tool kit according to claim 1, wherein said clamp is rigid with a measure of resilience.

8. A tool kit according to claim 1, wherein said approximator is scissors-like with gripping ends.

9. A tool kit according to claim 1, wherein said approximator is forceps-like, having arms with end portions capable each to hold a solid hemi-clamp.

* * * * *